(12) United States Patent
Salisbury et al.

(10) Patent No.: US 8,629,298 B2
(45) Date of Patent: Jan. 14, 2014

(54) ACETIC ACID PRODUCTION PROCESS

(75) Inventors: Brian A. Salisbury, Oxford, PA (US); Noel C. Hallinan, Loveland, OH (US)

(73) Assignee: Lyondell Chemical Technology, L.P., Houston, TX (US)

( * ) Notice: Subject to any disclaimer, the term of this patent is extended or adjusted under 35 U.S.C. 154(b) by 395 days.

(21) Appl. No.: 13/037,041

(22) Filed: Feb. 28, 2011

(65) Prior Publication Data

US 2012/0220801 A1 Aug. 30, 2012

(51) Int. Cl.
*C07C 51/12* (2006.01)

(52) U.S. Cl.
USPC ......................................... 562/519

(58) Field of Classification Search
None
See application file for complete search history.

(56) References Cited

U.S. PATENT DOCUMENTS

| 6,100,975 | A | 8/2000 | Smith | |
|---|---|---|---|---|
| 6,552,221 | B1 | 4/2003 | Hallinan | |
| 7,790,920 | B2 * | 9/2010 | Brtko et al. | 562/519 |
| 2007/0256510 | A1 * | 11/2007 | Buchs et al. | 73/865.3 |

OTHER PUBLICATIONS

S.E. Nave "Rugged Fiber Optic Probes and Sampling Systems for Remote Chemical Analysis Via the Raman Technique" ISA, Paper #96-042, pp. 453-467, 1996.*
PCT International Search Report and Written Opinion mailed Aug. 6, 2012, for PCT application No. PCT/US2012/026693.

* cited by examiner

*Primary Examiner* — Yevegeny Valenrod (57) ABSTRACT

A method for determining the characteristic of one or more components in a step of an acetic acid production process using Raman spectroscopy. The process includes providing a feed stream comprising multiple components to a separations unit, one of the components being acetic acid, the separations unit separating the feed stream into two or more exit streams having a different composition from one another, and measuring a characteristic of one or more of the components by Raman spectroscopic analysis.

13 Claims, 3 Drawing Sheets

ACETIC ACID PRODUCTION PROCESS

FIELD OF THE INVENTION

The present disclosure relates to monitoring components in an acetic acid preparation process. More particularly, the present disclosure relates to a method for measuring components by Raman spectroscopy in process steps downstream from an acetic acid reactor. Additionally, the disclosure relates to controlling an acetic acid production process in view of Raman spectroscopy measurements.

BACKGROUND OF THE INVENTION

Acetic acid is commercially produced by methanol carbonylation. Prior to 1970, acetic acid was made using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem associated with the original Monsanto process is that a large amount of water (about 14%) is needed to produce hydrogen in the reactor via the water-gas shift reaction ($CO+H_2O \rightleftharpoons CO_2+H_2$). Water and hydrogen are needed to react with precipitated Rh(III) and inactive Rh(III) species to regenerate the active Rh(I) catalyst. This large amount of water increases the amount of hydrogen iodide, which is highly corrosive and leads to engineering problems. Further, removing a large amount of water from the acetic acid product is costly.

In the late '70s, Celanese modified the carbonylation process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the early '90s, Millennium Petrochemicals developed a new rhodium carbonylation catalyst system that does not use iodide salt. The catalyst system uses a pentavalent Group VA oxide such as triphenylphosphine oxide as a catalyst stabilizer. The Millennium catalyst system not only reduces the amount of water needed but also increases the carbonylation rate and acetic acid yield. See U.S. Pat. No. 5,817,869.

In acetic acid processes measurement of the various components in the system has been used for controlling and monitoring the process. For example, U.S. Pat. No. 6,552,221 teaches process control for acetic acid manufacture using infrared spectroscopy. According to the '221 patent, samples are collected from columns and/or transfer lines downstream of a reactor vessel, and the concentration of one or more components in the sample is measured by an infrared analyzer. The concentration measurements are then used to make adjustments in the concentration of components in the reaction system, directly or indirectly, such as by adjusting the temperature profile in a particular column, the flow rate of solution in to or out of a column, the vent gas rate out of the reactor or a column, or the addition or extraction of a component to or from the solution. The components measured include water, acetic acid, methyl acetate, methyl iodide, aldehydes, hydrocarbons, propionic acid, and hydrogen iodide. Similarly, U.S. Pat. No. 6,362,366 teaches an online method to measure components in the reactor mixture.

Several drawbacks regarding the use of infrared spectroscopy with acetic acid processes have been found as disclosed herein, including large $H_2O$ and acetic acid absorbance values while having relatively weak MeI absorbance values. While large absorbances can be helpful in quantitation, in the acetic acid process, the absorbance values of $H_2O$ and acetic acid are so large that they have a tendency to overlap and interfere with absorbances of other components thereby making quantitation difficult. Additionally, a large number of calibration standards are required for acetic acid processes to obtain calibration models with acceptable accuracy. Moreover, infrared has drawbacks regarding hardware flexibility and implementation in a process environment.

There have been numerous infrared based studies carried out with regard to methanol (MeOH) carbonylation. In other processes, Raman spectroscopy has been employed. For example U.S. Pat. No. 6,100,975 used Raman spectroscopy for analyzing fluid streams containing petroleum products. However, Raman spectroscopy has not been heretofore disclosed by academic or patent literature for use in acetic acid processes, except in pending application Ser. No. 12/906,575, filed Oct. 18, 2010. Application Ser. No. 12/906,575 employs Raman spectroscopy to measure the concentration of a component in an acetic acid reaction mixture.

Similar to infrared, Raman is a form of vibrational spectroscopy. However, infrared bands are associated with light absorption and arise from a change in the dipole moment of a molecule. In contrast, Raman bands are associated with light scattering and arise from a change in polarizability of a molecule. While some molecules exhibit only Raman or only infrared vibrational transitions, others exhibit both Raman and infrared bands but with different intensities and selectivity. Accordingly, in an acetic acid process, it is unknown whether the components in the process will provide sufficiently observable spectra to determine concentration, and furthermore, in a multi-component system, some spectra may overlap therefore making observation difficult. Therefore, it is unknown whether Raman spectroscopy can be employed in a multi-component system such as an acetic acid production process to accurately measure various components.

What is needed is a system that is easily employable in an acetic acid process, which permits accurate measurement of the components without burdensome calibration standards.

SUMMARY OF THE INVENTION

The process and method disclosed herein includes determining the characteristic of one or more components in a step of an acetic acid production process. The method includes providing a feed stream having multiple components to a separations unit, one of the components being acetic acid, the separations unit separating the feed stream into two or more exit streams having a different composition from one another, and measuring a characteristic of one or more of the components in the separations unit by Raman spectroscopic analysis.

In further embodiments, the characteristic measured is concentration or density. In some embodiments, the separations unit can be a distillation column or decanter. Further, the one or more components can be in the light phase of the decanter or the light ends bottoms. The one or more components can be selected from the group consisting of methyl iodide, methyl acetate, water, acetic acid, hydrogen iodide, acetaldehyde, and mixtures thereof.

In other embodiments disclosed herein is a method for controlling an acetic acid production process. The process includes the steps of (i) reacting methanol and carbon monoxide in the presence of a carbonylation catalyst to produce a reactor product comprising acetic acid;

(ii) measuring the characteristic of one or more components in a separations unit downstream from said reactor by Raman spectroscopic analysis; and (iii) adjusting the conditions in a reactor or in any subsequent step of the acetic acid production process.

In some embodiments, adjusting the conditions can include modifying the temperature or flow rate of a feed, recycle or exit stream of a reactor or separations unit or modifying the temperature of a reactor or separations unit.

BRIEF DESCRIPTION OF THE DRAWINGS

Embodiments disclosed herein are described, by way of example only, with reference to the following figures.

DETAILED DESCRIPTION OF THE INVENTION

The present disclosure relates to a method for measuring components by Raman Spectroscopy in process steps downstream from an acetic acid reactor.

The acetic acid process involves the a carbonylation reaction performed in the presence of a carbonylation catalyst and a catalyst stabilizer. Suitable carbonylation catalysts include those known in the acetic acid industry. Examples of suitable carbonylation catalysts include rhodium catalysts and iridium catalysts. Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_3$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 4H_2O$, $IrBr_3 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates. The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are chloride-free such as acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydrolysis/methanolysis of polyvinyl acetate can be used for the carbonylation reaction.

Preferably, the reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

After the carbonylation reaction, the reaction mixture is passed downstream to a number of separation units. Separations unit may be defined herein as a vessel or step in an acetic acid process which separates a feed stream into two or more separate exit streams where the two exit streams differ from one another in some aspect. The separation can be based on methods known in the art such as separation by physical characteristics, such as density, volatility, boiling point, phase, absorbance, adsorbance and other characteristics used for separating chemical components known in the art.

In an acetic acid process, these units include, but are not limited to, a flash tank, a light ends distillation column, a decanter, drying column and a heavy ends distillation column. These units are discussed in turn as follows.

The acetic acid product stream is withdrawn from the reactor and is separated, by a flash separation via a flash tank, into a liquid fraction comprising the catalyst and the catalyst stabilizer and a vapor fraction comprising the acetic acid product, the reactants, water, methyl iodide, and impurities generated during the carbonylation reaction including acetaldehyde. The liquid fraction is preferably recycled to the carbonylation reactor. The vapor fraction is then passed to a distillation column.

The distillation column, the so called "light ends distillation," separates an overhead comprising methyl iodide, water, methanol, methyl acetate, and acetaldehyde from an acetic acid stream comprising acetic acid, a small amount of water, and heavy impurities such as propionic acid. The acetic acid stream may be passed to a drying column to remove water and then be subjected to the so called "heavy ends distillation" to remove the heavy impurities.

As known in the art, the light ends distillation column separates the feed into two or more exit streams according to boiling point, including an overhead exit stream and a bottoms exit stream. The overhead from the light-ends distillation preferably comprises from about 30 wt % to about 70 wt % of methyl iodide (MeI), from about 5 wt % to about 15 wt % of methyl acetate (MeOAc), from about 5 wt % to about 35 wt % of acetic acid (HOAc), 10 wt % to about 40 wt % water ($H_2O$), from about 1 wt % to about 10 wt % of alkanes, and about 2 wt % or less of acetaldehyde (HAc) based on the total weight of the overhead. The bottoms contains about 80 wt % to about 100 wt % of acetic acid, about 3 wt % to about 20 wt % water, and about from 0 wt % to about 3 wt % Hydrogen Iodide (HI).

The overhead is condensed and separated by density in a decanter unit to a light, aqueous phase and a heavy, organic phase. The light, aqueous phase comprises water, from about 20 wt % to about 80 wt %, acetic acid, from about 20 wt % to about 80 wt %, methyl acetate, from about 0 wt % to about 10 wt %, methyl Iodide, from about 0 wt % to about 10 wt %, acetaldehyde, from about 0 wt % to about 2 wt %, and preferably 0 wt % alkanes. The density of the light phase is preferably 1.0 to 1.10 $g/cm^3$. The aqueous phase is usually disposed in the upper portion of the decanter, whereas the heavy, organic phase is disposed toward the bottom portion of the decanter. The heavy, organic phase comprises water, from about 0 wt % to about 2 wt %, acetic acid, from about 0 wt % to about 10 wt %, methyl acetate, from about 0 wt % to about 20 wt %, methyl Iodide, from about 60 wt % to about 95 wt %, acetaldehyde, from about 0 wt % to about 2 wt %, other alkanes, from 0 to 15 wt %. The density of the heavy phase is 1.4 to 2.2 $g/cm^3$. The light, aqueous phase is preferably recycled to the reactor or to the light ends distillation.

The method disclosed herein involves measuring a component of a separations unit downstream from the acetic reactor by Raman spectroscopy. Raman spectroscopy is known, for instance, see U.S. Pat. No. 7,505,127. The Raman shift occurs when light impinges upon a molecule and interacts with the electron cloud and the bonds of that molecule. A photon excites the molecule from the ground state to a virtual energy state. When the molecule relaxes it emits a photon and it returns to a different rotational or vibrational state. The difference in energy between the original state and this new state leads to a shift in the emitted photon's frequency away from the excitation wavelength. Raman spectra are typically shown as plots of intensity (arbitrary units) versus Raman shift. Raman shifts are typically expressed in wavenumbers, which have units of inverse length. Most commonly, the units chosen for expressing wavenumber in Raman spectra is inverse centimeters ($cm^{-1}$).

The instrumentation used to collect and process Raman data includes a Raman spectrometer system, a transmittance system, a control loop, and a processor. The Raman spectrometer system comprises a Raman spectrometer, the principal components of which are light source, a monochromator, and a detector. The light source delivers excitation radiation to the probe. Scattered radiation is collected, filtered of Raleigh scattered light, and dispersed via a monochromator. The dispersed Raman scattered light is then imaged onto a detector and subsequently processed within the processor.

Typically, the light source is a visible laser, such as a frequency-doubled Nd:YAG laser (532 nm), a helium-neon laser (633 nm), or a solid-state diode laser (such as 785 nm). The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used.

The excitation radiation can be delivered to the probe, and the scattered radiation collected from the probe by any convenient means known in the art, such as conventional beam manipulation optics or fiber optic cables generally designated. For an on-line process measurement, it is particularly convenient to deliver the excitation radiation and collect the scattered radiation through fiber optic cables. It is a particular advantage of Raman spectroscopy that the excitation radiation typically used is readily manipulated fiber optically, and thus the excitation source can be positioned remotely from the sampling region. Thus Raman spectroscopy has an advantage over prior infrared systems in that it can facilitate physical employment in an acetic acid process plant.

The scattered radiation is collected and dispersed by any convenient means known in the art, such as a fiber optic probe. The collected scattered radiation is filtered to remove Raleigh scattering and then frequency (wavelength) dispersed using a suitable dispersive element, such as a blazed grating or a holographic grating, or interferometrically (e.g., using Fourier transforms). The grating can be fixed or scanning, depending upon the type of detector used. The monochromator can be any such dispersive element, along with associated filters and beam manipulation optics.

The dispersed Raman scattering is imaged onto a detector. Typical detectors include array detectors generally used with fixed-dispersive monochromators, such as diode arrays or charge coupled devices (CCDs), or single element detectors generally used with scanning-dispersive monochromators or FT-based spectrometers, such as lead sulfide detectors and indium-gallium-arsenide detectors. In the case of array detectors, the detector is calibrated such that the frequency (wavelength) corresponding to each detector element is known. The detector response is delivered to the processor that generates a set of frequency shift, intensity (x,y) data points which constitute the Raman spectrum.

The scattered radiation of the carbonylation reaction mixture may be collected by a probe in a variety of locations in each of the separations units. The probe may be placed directly in a vessel, or a feed stream entering or exiting the unit, or a slip stream. For example when measuring the decanter, the probe can be placed directly into the upper portion of the unit or in a stream exiting the top of the unit. When measuring the light ends bottoms, the probe can be placed directly into the lower portion of the unit containing the bottoms, or an exit stream from the unit. Also exit streams can have the same or similar concentration as the portion of the unit it is exiting from, and accordingly, measuring such component concentrations are considered the same as if measuring directly in the respective top or bottom portion of the unit. Alternatively, the probe does not contact with the liquid mixture. The probe delivers the excitation radiation from the light source to the reactor mixture liquid, collects the scattered radiation, and delivers the scattered radiation to the monochromator through the transmittance system. There are multiple ways for obtaining measurements using Raman spectroscopy of the units in the acetic acid process which are not limited herein.

In one embodiment, the method disclosed herein includes measuring the concentration or density of one or more components in a separations unit of the acetic acid process and adjusting the conditions in the reactor or in any subsequent step of the acetic acid production process in response to the measured concentration. For example, the temperature or pressure of the reactor or other separations units can be increased or decreased. Additionally, the flow rates of the feeds or exit streams can be increased or decreased. Such adjustments can affect the concentrations of the one or more components in the separations units or reactor in order to bring them within the desired range, for example, the ranges for the decanter and light ends column are provided above. Alternatively or additionally, one or more components can be measured in the separations units to adjust the particular concentration of a component in order to optimize the process or a particular separations unit. Moreover, the concentration of a particular component or density can indicate that the process is not optimized or that a particular variable, such as temperature, pressure of a unit or flow rate of a feed/exit stream is outside of a predetermined range and should be corrected.

For infrared spectroscopy, calibration for accurate MeI concentration prediction is difficult to achieve. Furthermore, $H_2O$ and acetic acid have relatively large infrared absorbances which interfere with other components, while MeI has a relatively weak absorbance. Furthermore, systems with high amounts acetic as well as $H_2O$ are more problematic for calibrating and obtaining an accurate concentration measurement.

As disclosed herein, it has been found that Raman spectroscopy can be used in process steps of an acetic acid production process and accordingly controlling or adjusting the process based on such measurements. In particular, components in separation units downstream from the acetic acid may be measured by Raman Spectroscopy. These units include, but are not limited to, flash tanks, distillation columns, including both "light ends" and "heavy ends" columns, a decanter, and a drying column.

Raman shifts for several components contained in the light phase portion of the decanter are as follows:

TABLE 1

Decanter - Light Phase

| Component | Raman shift(s), $cm^{-1}$ |
|---|---|
| MeI | 525 |
| MeOAc | 857, 641 |
| $H_2O$ | 3250 |
| HOAc | 2942, 1698, 1432, 1361, 1246, 1014, 892, 576 |
| HAc | 1119 |
| Density | 3500 - 100 |

Raman shifts for several components contained in the light ends distillation column bottoms are as follows:

TABLE 2

Raman Light Ends Distillation Column Bottoms

| Component | Raman shift(s), $cm^{-1}$ |
|---|---|
| $H_2O$ | 1703, 460 |
| HOAc | 2942, 1757, 1433, 1367, 892, 521 |
| HI | 111 |

Figure 1:
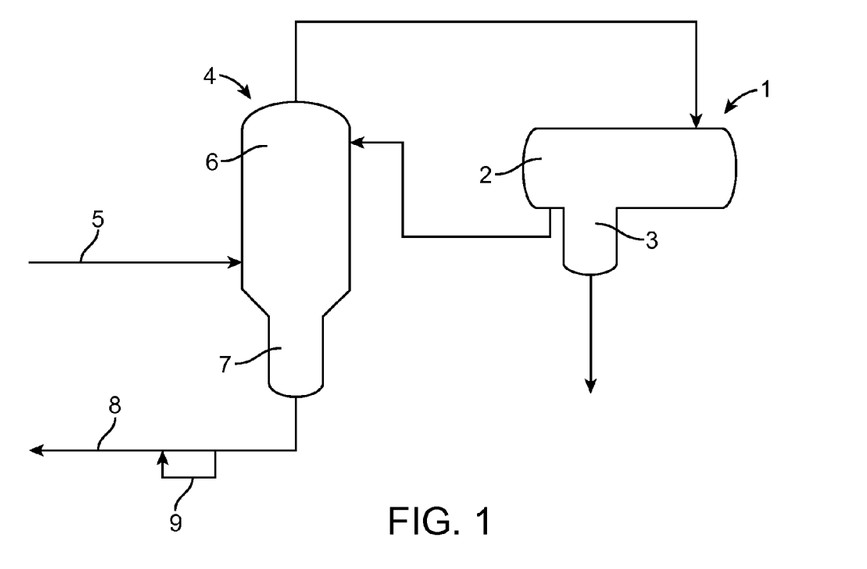
FIG. 1 illustrates one embodiment of several steps in an acetic acid process.

Referring now to FIG. 1, a decanter 1 and a "light ends" distillation column 4 is shown. With respect to the decanter 1, a gas phase stream is provided from the top of the light ends 4 to the decanter 1. The decanter 1 has two portions, namely a light phase 2 with lower density in the upper portion and a heavy phase 3 with higher density contained in the lower portion of the decanter 1, also known as "the boot." The Raman probe can be inserted into the light phase 2 mixture of the decanter 1 for measuring components. Preferably, the components measured in the light phase of the decanter include those in Table 1, namely MeI, $H_2O$, HOAc, HAc, MeOAc, as well as the density of the mixture. The probe can also be placed also in the gas phase just above the light liquid phase for measuring the desired light phase components. Generally the heavy phase in the decanter need not be measured.

Additionally in FIG. 1 is shown a "light ends" distillation column 4. The light ends receive a feed 5 from a unit further upstream, for example a flash tank (not shown). The upper portion 6 of the light ends column has lighter components (lower boiling point) where a gaseous overhead is taken from the top of the column. In the lower portion of the column a bottoms 7 containing heavier components (higher boiling point) is exited from the column in stream 8. A Raman probe can be placed in the bottoms 7 of the column or in the stream 8 to measure components of interest. Additionally, a slip stream 9 can be provided which receives a portion of the stream 8 for measuring with a Raman spectrometer. It will be understood that the concentrations of the components in the bottoms 7 of the column will be the same or approximately the same whether measured in the stream 8, slip stream 9 or bottoms 7. The preferred components measured in the light ends column are those noted in Table 2, namely $H_2O$, HOAc, HI.

EXAMPLES

Methods

To identify the Raman shifts and intensities of components a number of experiments are performed (approximately 10-20 standards) for each sample type in which the concentration of said component varies while the concentrations of other components remain essentially constant or under such conditions that the other components will not interfere with the measurement of said component. These experiments are performed by preparation of multi-component standards in 20 mL sample vials at room temperature and atmospheric pressure.

It should be noted that the appropriate Raman shift region used for quantitatively analyzing a particular component may vary depending on the vessel or stream in which it is being analyzed, given that a particular component may be more concentrated in one location in the process as compared to its concentration at another location and that a particular component's Raman peak will be interfered with to varying degrees depending on the sample type.

Spectroscopic data were collected using a Thermo Nicolet Almega-XR dispersive Raman spectrometer operating at 532 nm. For each sample, 32 spectra are collected and averaged over the range 100-4250 cm$^{-1}$. Each spectrum had an acquisition time of 1 second, and spectral resolution was 4 cm$^{-1}$.

Multi-component standards were prepared for the decanter light phase and the light ends distillation column bottoms. For the decanter, 17 multi-component standards were prepared, with 14 used for calibration and 3 used for validation. For the light ends column, 15 multi-component standards were prepared, 12 for calibration and 3 for validation. Calibration models were generated using TQ Analyst calibration software from Thermo Scientific. Validation was tested by comparison of the values predicted by the model with actual values.

Decanter

In contrast to infrared, which requires about 100 standards, only 17 multicomponent standards were prepared and analyzed for the decanter light phase. The standards which were prepared are shown in Table 3 as follows (tables 3-5, 7-10 in wt %):

TABLE 3

Decanter Light Phase Multicomponent Standards

| Sample | HAc | H$_2$O | HOAc | MeOAc | MeI | Density |
|---|---|---|---|---|---|---|
| Std #1 | 0.00 | 16.69 | 76.40 | 0.00 | 6.91 | 1.081 |
| Std #2 | 1.39 | 19.13 | 71.92 | 3.87 | 3.69 | 1.051 |
| Std #3 | 1.80 | 24.68 | 63.76 | 4.93 | 4.82 | 1.051 |
| Std #4 | 2.52 | 34.41 | 49.47 | 6.86 | 6.74 | 1.052 |
| Std #5 | 0.88 | 37.38 | 54.95 | 1.12 | 5.66 | 1.058 |
| Std #6 | 0.54 | 46.75 | 47.05 | 1.50 | 4.15 | 1.045 |
| Std #7 | 0.37 | 53.75 | 37.90 | 7.49 | 0.49 | 1.014 |
| Std #6 | 1.22 | 56.17 | 35.72 | 3.47 | 3.42 | 1.031 |
| Std #9 | 1.70 | 62.87 | 27.79 | 4.74 | 2.89 | 1.022 |
| Std #10 | 0.15 | 77.74 | 21.41 | 0.52 | 0.18 | 1.011 |
| Std #11 | 0.86 | 52.78 | 37.82 | 7.52 | 1.01 | 1.016 |
| Std #12 | 0.00 | 54.55 | 38.00 | 7.44 | 0.00 | 1.013 |
| Std #13 | 0.00 | 13.68 | 80.70 | 0.00 | 5.62 | 1.075 |
| Std #14 | 1.55 | 21.38 | 68.51 | 4.31 | 4.25 | 1.052 |
| Std #15 | 0.49 | 46.06 | 47.76 | 1.41 | 4.29 | 1.046 |
| Std #16 | 0.92 | 51.92 | 40.78 | 2.58 | 3.80 | 1.038 |
| Std #17 | 0.24 | 77.55 | 21.61 | 0.31 | 0.30 | 1.011 |

Figure 2:
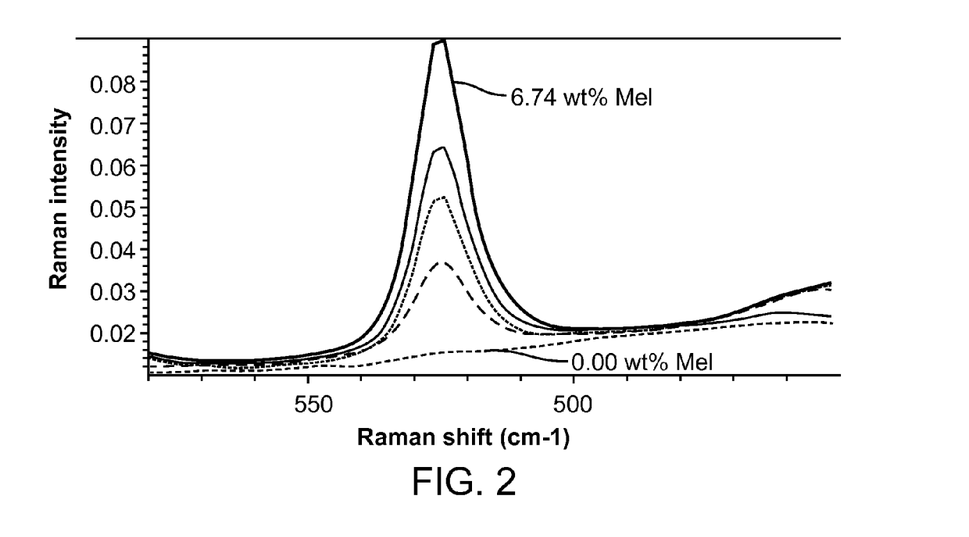
FIG. 2 illustrates Raman overlaid spectra of several of decanter light phase standards in which a spectral region with a fully resolved MeI signal is shown.
Figure 3:
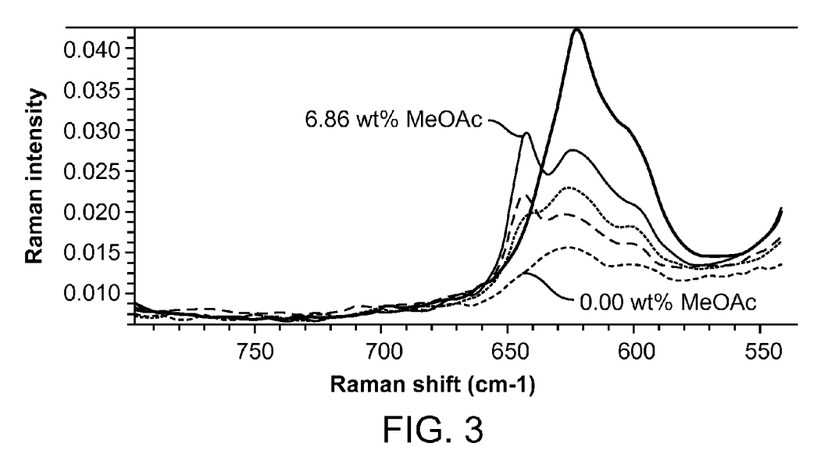
FIG. 3 illustrates Raman overlaid spectra of several of decanter light phase standards in which a spectral region with a fully resolved MeOAc signal is shown.

Raman overlaid spectra of several of these decanter light phase standards are provided in FIG. 2 in which a spectral region with a fully resolved MeI signal is shown. Similarly, a signal for MeOAc is observed in a different spectral region as shown in FIG. 3.

Figure 4:
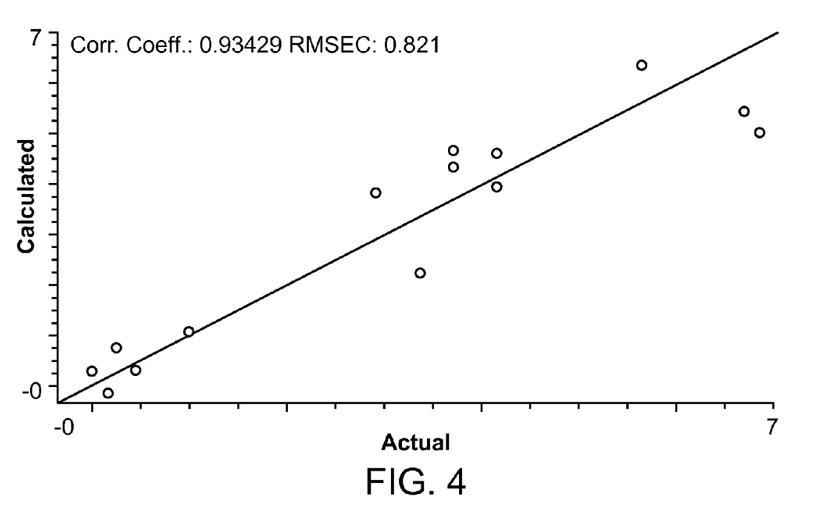
FIG. 4 illustrates an Infrared 5 factor calibration model for decanter light phase for component MeI.
Figure 5:
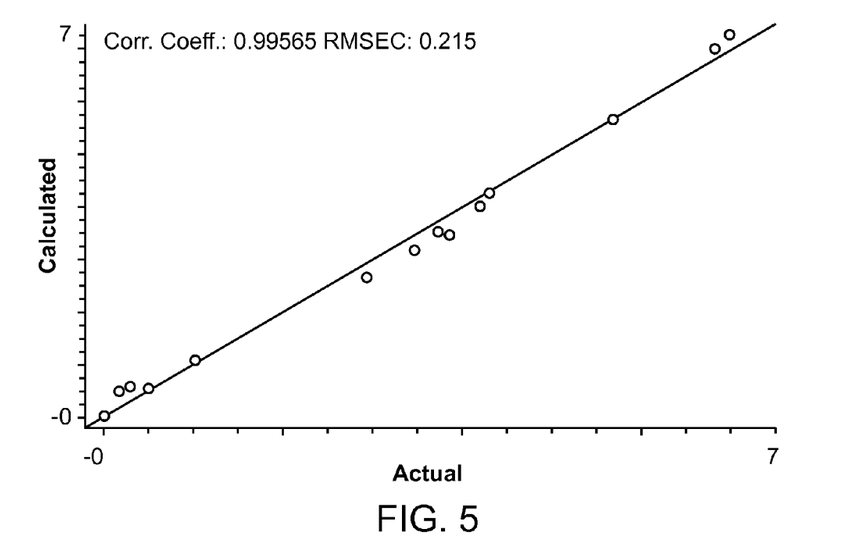
FIG. 5 illustrates a 2 factor Raman calibration model for decanter light phase for component MeI.

In order to directly compare the accuracy of the existing infrared calibration model which contains over 100 standards with a Raman model, 14 of the standards in Table 3 were measured according to Raman spectroscopy. A subset of infrared spectra associated with 14 of the calibration standards of approximate compositions as shown in Table 3 was also identified and re-modeled. The contrast between the resulting infrared and Raman calibration models for MeI is evident from FIGS. 4 and 5. FIG. 4 displays an Infrared 5 factor calibration model for decanter light phase for component MeI. FIG. 5 shows a Raman 2 Factor calibration model for a decanter light phase for component MeI. As can be seen, FIG. 5 Raman spectroscopy produces a superior model over the infrared model shown in FIG. 4. Additionally, only 2 factors are required for the Raman model in contrast to the 5 for the Infrared model.

Subsequent to calibration, three of the standards shown in Table 3 above that were not used to prepare the calibration model were used as validation standards. Predicted infrared and Raman values for all components are shown in Tables 4 and 5 below.

TABLE 4

Raman Validation

| Sample | HAc Act | HAc Pred | H2O Act | H2O Pred | HOAc Act | HOAc Pred | MeOAc Act | MeOAc Pred | MeI Act | MeI Pred | Den Act | Den Pred | Mat Bal |
|---|---|---|---|---|---|---|---|---|---|---|---|---|---|
| Std #3 | 1.8 | 1.85 | 24.64 | 24.59 | 63.82 | 64.7 | 4.92 | 4.93 | 4.82 | 4.98 | 1.051 | 1.053 | 101.05 |
| Std #5 | 0.88 | 0.74 | 37.35 | 37.75 | 54.99 | 54.69 | 1.09 | 1.17 | 5.66 | 5.82 | 1.058 | 1.059 | 100.17 |
| Std #15 | 0.49 | 0.52 | 46.08 | 45.99 | 47.79 | 47.73 | 1.41 | 1.47 | 4.29 | 4.21 | 1.046 | 1.046 | 99.92 |

TABLE 5

FTIR Validation

| Sample | HAc Act | HAc Pred | H2O Act | H2O Pred | HOAc Act | HOAc Pred | MeOAc Act | MeOAc Pred | MeI Act | MeI Pred | Den Act | Den Pred | Mat Bal |
|---|---|---|---|---|---|---|---|---|---|---|---|---|---|
| Std #3 | 1.8 | 1.84 | 24.64 | 24.59 | 63.82 | 64.22 | 4.92 | 4.91 | 4.82 | 4.51 | 1.051 | 1.055 | 100.07 |
| Std #5 | 0.88 | 1.03 | 37.35 | 37.95 | 54.99 | 56.17 | 1.09 | 0.88 | 5.66 | 3.48 | 1.058 | 1.044 | 99.51 |
| Std #15 | 0.49 | 0.45 | 46.08 | 44.83 | 47.79 | 47.59 | 1.4 | 1.18 | 4.29 | 5.06 | 1.046 | 1.035 | 99.11 |

Approximate accuracies were obtained by calculating the average wt % differential between actual and calculated values shown in Tables 4 and 5, and which are displayed in Table 6.

TABLE 6

| Technique | HAc | H₂O | HOAc | MeOAc | MeI | Density |
|---|---|---|---|---|---|---|
| Raman | 0.07 | 0.18 | 0.41 | 0.05 | 0.13 | 0.001 |
| Infrared | 0.08 | 0.63 | 0.59 | 0.15 | 1.09 | 0.01 |

As can be seen, it is surprisingly shown that Raman produces more accurate concentration measurements.

Light Ends Distillation Column

For the Light ends column bottoms, 15 standards are prepared. The standards prepared for Raman Spectroscopy are shown in Table 7 as follows:

TABLE 7

Raman Light Ends Bottoms Multicomponent Standards

| Simple | H₂O | HOAc | HI |
|---|---|---|---|
| Std #18 | 19.57 | 79 | 1.43 |
| Std #19 | 18.51 | 81.49 | 0 |
| Std #20 | 17.83 | 81.13 | 1.04 |
| Std #21 | 15.48 | 83.98 | 0.54 |
| Std #22 | 13.52 | 85.79 | 0.69 |
| Std #23 | 12.72 | 87.05 | 0.23 |
| Std #24 | 12.58 | 85.42 | 2 |
| Std #25 | 10.31 | 87.29 | 2.4 |
| Std #26 | 7.88 | 90.4 | 1.72 |
| Std #27 | 4.27 | 95.36 | 0.37 |
| Std #28 | 3.91 | 95.8 | 0.29 |
| Std #29 | 7.4 | 92.6 | 0 |
| Std #30 | 6.76 | 92.9 | 0.35 |
| Std #31 | 10.16 | 89.66 | 0.18 |
| Std #32 | 5.05 | 93.44 | 1.51 |

Figure 6:
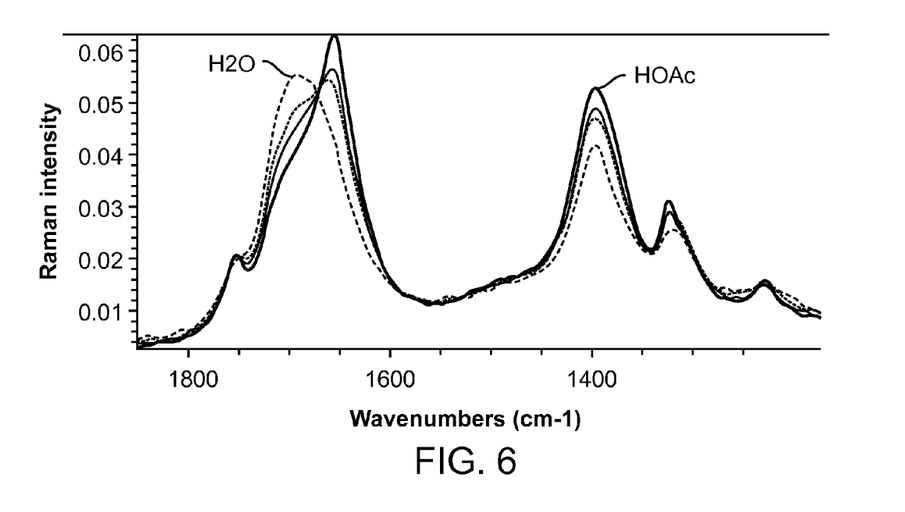
FIG. 6 illustrates Raman overlaid spectra of several of light ends bottoms standards with clear signals from $H_2O$ and HOAc.

Raman overlaid spectra of several of these light ends bottoms standards are provided in FIG. 6, which shows clear signals from H₂O and HOAc.

Standards were prepared for infrared analysis as well, as shown in Table 8:

TABLE 8

Infrared Light Ends Bottoms Multicomponent Standards

| Standard | H₂O wt % | HOAc wt % | HI wt % |
|---|---|---|---|
| Std #33 | 19.86 | 78.61 | 1.53 |
| Std #34 | 18.49 | 81.51 | 0.00 |
| Std #35 | 17.96 | 81.12 | 0.92 |
| Std #36 | 15.56 | 84.04 | 0.40 |
| Std #37 | 13.49 | 85.84 | 0.67 |
| Std #38 | 12.71 | 87.12 | 0.17 |
| Std #39 | 12.55 | 85.55 | 1.91 |
| Std #40 | 9.96 | 87.71 | 2.34 |
| Std #41 | 7.53 | 90.82 | 1.65 |
| Std #42 | 4.07 | 95.57 | 0.36 |
| Std #43 | 3.91 | 95.79 | 0.30 |
| Std #44 | 7.41 | 92.59 | 0.00 |
| Std #45 | 6.96 | 92.70 | 0.35 |
| Std #46 | 9.81 | 90.06 | 0.13 |
| Std #47 | 4.88 | 93.58 | 1.54 |

Three of the standards shown in Tables 7 and 8 which had not been used to prepare the calibration models were used as validation standards. Predicted infrared and Raman values for all components are shown in Tables 9 and 10 below (All values shown in wt %).

TABLE 9

Raman Validation

| Sample | H₂O Act | H₂O Pred | HOAC Act | HOAc Pred | HI Act | HI Pred |
|---|---|---|---|---|---|---|
| Std # 20 | 17.83 | 18.26 | 81.13 | 81.04 | 1.04 | 1.02 |
| Std # 24 | 12.58 | 12.76 | 85.42 | 85.12 | 2 | 1.85 |
| Std # 29 | 7.4 | 7.17 | 92.6 | 92.6 | 0 | 0 |

TABLE 10

FTIR Validation of LEB

| Sample | H₂O Act | H₂O Pred | HOAc Act | HOAc Pred | HI Act | HI Pred |
|---|---|---|---|---|---|---|
| Std #35 | 17.96 | 18.22 | 81.12 | 80.45 | 0.92 | 1.03 |
| Std #39 | 12.55 | 12.56 | 85.55 | 85.4 | 1.91 | 0.01 |
| Std #44 | 7.41 | 7.83 | 92.59 | 91.72 | 0 | 0.29 |

Approximate accuracies were obtained by calculating the average wt % differential between actual and calculated values are shown in Tables 9 and 10, and which are displayed in Table 11.

TABLE 11

| Technique | H₂O | HOAc | HI |
|---|---|---|---|
| Raman | 0.28 | 0.13 | 0.06 |
| Infrared | 0.23 | 0.56 | 0.14 |

As can be seen, it is surprisingly shown that Raman produces more accurate concentration measurements for HOAc and HI.

What is claimed is:

1. A method for measuring a component of a separations unit downstream from the acetic acid reactor comprising:
   (i) directing a feed stream to a separations unit, wherein the feed stream comprises the following components:
   methyl iodide,
   water,
   methanol,
   methyl acetate,
   acetaldehyde,
   acetic acid,
   alkanes and
   propionic acid,
   (ii) separating the feed stream in the separating unit into an overhead exit stream and a bottoms exit stream
   wherein the overhead exit stream comprises the following components:
   30 wt. % to about 70 wt. % methyl iodide,
   10 wt. % to about 40 wt. % water,
   5 wt. % to about 15 wt. % methyl acetate,
   less than 2 wt. % acetaldehyde,
   5 wt. % to about 35 wt. % acetic acid,
   1 wt. % to about 10 wt. % alkanes and
   wherein the bottoms exit stream comprises the following components:
   80 wt. % to 100 wt. % acetic acid,
   3 wt. % to about 20 wt. % water; and
   measuring a characteristic of one or more said components in said separations unit by Raman spectroscopic analysis.

2. The method of claim 1, wherein the characteristic measured is concentration or density.

3. The method of claim 1, wherein the separations unit is a distillation column or a decanter.

4. The method of claim 3, wherein the characteristic of one or more components in a light phase of the decanter is measured.

5. The method of claim 3, wherein the characteristic of one or more components in the distillation column bottoms is measured.

6. A method for controlling an acetic acid production process, comprising:
   (i) reacting methanol and carbon monoxide in the presence of a carbonylation catalyst to produce a reactor product comprising acetic acid;
   (ii) separating the reactor product in a separating unit into an overhead exit stream and a bottoms exit stream wherein the overhead exit stream comprises the following components:
      30 wt. % to about 70 wt. % methyl iodide,
      10 wt. % to about 40 wt. % water,
      5 wt. % to about 15 wt. % methyl acetate,
      less than 2 wt. % acetaldehyde,
      5 wt. % to about 35 wt. % acetic acid,
      1 wt. % to about 10 wt. % alkanes and
   wherein the bottoms exit stream comprises the following components:
      80 wt. % to 100 wt. % acetic acid,
      3 wt. % to about 20 wt. % water;
   (iii) measuring the characteristic of one or more components in a separations unit downstream from said reactor by Raman spectroscopic analysis; and
   (iv) adjusting the conditions in a reactor or in any subsequent step of the acetic acid production process.

7. The method of claim 6, wherein the separations unit is a distillation column or a decanter.

8. The method of claim 6, wherein the characteristic of one or more components in a light phase of the decanter is measured.

9. The method of claim 6, wherein the characteristic of one or more components in the distillation column bottoms is measured.

10. The method of claim 6, wherein said adjusting the conditions comprises modifying the temperature or flow rate of a feed, recycle or exit stream of a reactor or separations unit or modifying the temperature of a reactor or separations unit.

11. The method of claim 6, wherein the catalyst is a rhodium catalyst.

12. The method of claim 6, wherein the reaction occurs in the presence of a catalyst stabilizer selected from the group consisting of pentavalent Group VA oxides, metal iodide salts, and mixtures thereof.

13. The method of claim 9, wherein the catalyst stabilizer is a phosphine oxide.

* * * * *

UNITED STATES PATENT AND TRADEMARK OFFICE
CERTIFICATE OF CORRECTION

PATENT NO. : 8,629,298 B2
APPLICATION NO. : 13/037041
DATED : January 14, 2014
INVENTOR(S) : Brian A. Salisbury and Noel C. Hallinan It is certified that error appears in the above-identified patent and that said Letters Patent is hereby corrected as shown below:

In the Drawings:

| | | |
|---|---|---|
| Sheet 1 of 3 | FIG. 2 | Delete "(cm-1)" and insert --($cm^{-1}$)-- |
| Sheet 2 of 3 | FIG. 3 | Delete "(cm-1)" and insert --($cm^{-1}$)-- |
| Sheet 3 of 3 | FIG. 6 | Delete "(cm-1)" and insert --($cm^{-1}$)-- |

In the Specification:

| | | |
|---|---|---|
| Column 3, | Line 39 | After "the", delete "a" |
| Column 10, | Table 4, Line 2 | Delete "H2O" and insert --$H_2O$-- |
| Column 10, | Table 4, Line 2 | Delete "H2O" and insert --$H_2O$-- |
| Column 10, | Table 5, Line 2 | Delete "H2O" and insert --$H_2O$-- |
| Column 10, | Table 5, Line 2 | Delete "H2O" and insert --$H_2O$-- |

Signed and Sealed this
Second Day of August, 2016

Michelle K. Lee
*Director of the United States Patent and Trademark Office*